United States Patent
Jiang et al.

(10) Patent No.: US 10,487,063 B2
(45) Date of Patent: Nov. 26, 2019

(54) PREPARATION METHOD FOR 1-SUBSTITUTED-1H-1,2,3-TRIAZOLE 4-CARBOXYLIC ACID

(71) Applicant: ABA CHEMICALS (SHANGHAI) LIMITED, Shanghai (CN)

(72) Inventors: Yueheng Jiang, Shanghai (CN); Limin Que, Shanghai (CN); Jun Xu, Shanghai (CN); Dongguang Qin, Shanghai (CN); Tong Cai, Shanghai (CN)

(73) Assignee: ABA CHEMICALS (SHANGHAI) LIMITED, Shanghai (CN)

( * ) Notice: Subject to any disclaimer, the term of this patent is extended or adjusted under 35 U.S.C. 154(b) by 67 days.

(21) Appl. No.: 15/547,516

(22) PCT Filed: Sep. 16, 2015

(86) PCT No.: PCT/CN2015/089699
§ 371 (c)(1),
(2) Date: Jul. 31, 2017

(87) PCT Pub. No.: WO2016/062175
PCT Pub. Date: Apr. 28, 2016

(65) Prior Publication Data
US 2018/0029999 A1    Feb. 1, 2018

(51) Int. Cl.
*C07D 249/04*    (2006.01)

(52) U.S. Cl.
CPC .................................. *C07D 249/04* (2013.01)

(58) Field of Classification Search
None
See application file for complete search history.

(56) References Cited

FOREIGN PATENT DOCUMENTS

CN    102408386    *    4/2012    ........... C07D 249/04

* cited by examiner

*Primary Examiner* — Alicia L Otton
(74) *Attorney, Agent, or Firm* — George G. Wang; Bei & Ocean

(57) ABSTRACT

Provided is a preparation method for 1-substituted-1H-1,2,3-triazole-4-carboxylic acid. 1-Substituted-4,5-dibromo-1H-1,2,3-triazole is added to an isopropylmagnesium chloride to obtain 1-substituted-4-bromo-1H-1,2,3-triazole by a reaction; then an isopropylmagnesium chloride-lithium chloride composite is added directly to obtain a mixture of 1-substituted-1H-1,2,3-triazole-4-carboxylic acid and 1-substituted-4-bromo-1H-1,2,3-triazole-5-carboxylic acid; secondly, to the mixture, a base and iodomethane are added to obtain 1-substituted-4-bromo-1H-1,2,3-triazole-5-carboxylic acid methyl ester by a reaction; the aqueous layer is adjusted with hydrochloric acid to pH=1-5, extracted with an organic solvent and dried; then 1-substituted-1H-1,2,3-triazole-4-carboxylic acid is obtained by concentration and crystallization. The method is suitable for industrialized production and has a greater application value.

9 Claims, No Drawings

PREPARATION METHOD FOR 1-SUBSTITUTED-1H-1,2,3-TRIAZOLE 4-CARBOXYLIC ACID

TECHNICAL FIELD

The Invention relates to the field of organic chemistry, particularly to the preparation method for organic compounds, and specifically to a preparation method for 1-substituted-1H-1,2,3-triazole-4-carboxylic acid.

BACKGROUND ART 1-substituted-1H-1,2,3-triazole-4-carboxylic acid is a new type of compound worth being developed. Having great potential in applications, the compound with triazole as the mother nucleus is a key midbody for preparing such many compounds as medicines, herbicides and insecticides and also a major pharmacophore in many pharmaceutical molecules. Therefore, 1-substituted-1H-1,2,3-triazole-4-carboxylic acid is a key midbody for preparing organic compounds, which is expressed as follows:

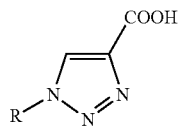

WO2008016192 has reported a preparation method for 1-methyl-1H-1,2,3-triazole-4-carboxylic acid, which is obtained through hydrolyzation of 1-methyl-1H-1,2,3-triazole-4-carboxylic acid ethyl ester under the action of alkali.

The reaction equation is as follows:

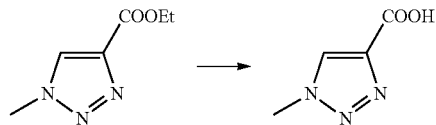

Refer to Applied Organometallic Chemistry, 25(8), 620-625, 2011 for the preparation method for 1-methyl-1H-1,2,3-triazole-4-carboxylic acid ethyl ester.

The reaction equation is as follows:

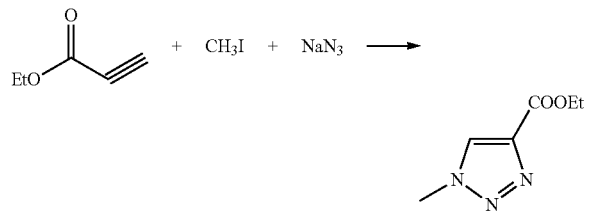

As the raw materials used in the method, propiolic acid ethyl ester is expensive and sodium azide is highly toxic and explosive.

As the method has such defects as expensive raw materials, demanding reaction equipment and non-environmental protection, it is not suitable for industrialized production. Therefore, it is urgent to improve the preparation method for 1-substituted-1H-1,2,3-triazole-4-carboxylic acid.

SUMMARY OF THE INVENTION

The purpose of the Invention is to overcome the above defects and develop and design a preparation method for 1-substituted-1H-1,2,3-triazole-4-carboxylic acid with simple operation, high yield and suitable for industrialized production.

Therefore, it provides a high-efficient preparation method for 1-substituted-1H-1,2,3-triazole-4-carboxylic acid.

The method comprises the following steps as:

1) Dissolving 1-substituted-4,5-dibromo-1H-1,2,3-triazole II in tetrahydrofuran (THF) or methyltetrahydrofuran (METHF) with a mass-to-volume ratio of 1:2-50 and cooling it to $-78°$ C.-$0°$ C.; adding a Grignard reagent isopropylmagnesium chloride and stirring for 0.5-2 h; then adding low alcohol of $C_1$-$C_4$ to obtain 1-substituted-4-bromo-1H-1,2,3-triazole III; adding a Grignard reagent isopropylmagnesium chloride-lithium chloride composite directly into the product without separation; heating up to $10°$ C.-$50°$ C. and stirring for 0.5-2 h; cooling it to $-30°$ C.-$0°$ C.; inletting carbon dioxide for 5-30 min and heating up to $20°$ C.-$25°$ C.; adjusting pH value to 1-5 with hydrochloric acid and then extracting it once or twice through the organic solvent with a weight-to-volume ratio of 1-20 times; drying it with anhydrous magnesium sulfate or anhydrous sodium sulfate and concentrating it up to dryness under reduced pressure at $40°$ C.-$50°$ C., thus a mixture of 1-substituted-1H-1,2,3-triazole-4-carboxylic acid I and 1-substituted-4-bromo-1H-1,2,3-triazole-5-carboxylic acid IV is obtained;

2) Dissolving the mixture of 1-substituted-1H-1,2,3-triazole-4-carboxylic acid I and 1-substituted-4-bromo-1H-1,2,3-triazole-5-carboxylic acid IV obtained in Step (1) in the mixed solvent of THF/METHF and N,N-dimethylformamide/N,N-dimethylacetamide with a volume ratio of 1-99%: 99-1%; adding inorganic or organic alkali and methyl iodide for reaction at $0°$ C.-$80°$ C. for 5-48 h; after the reaction, adding the mixture of water and organic solvent with a mass-to-volume ratio of 1:1-20 at $20°$ C.-$25°$ C. for layering (the volume ratio of water and organic solvent is 10-1:1-10); drying the organic layer with anhydrous magnesium sulfate or anhydrous sodium sulfate and then filtering out the drying agent; concentrating the organic solvent up to dryness under reduced pressure at $40°$ C.-$50°$ C., thus 1-substituted-4-bromo-1H-1,2,3-triazole-5-carboxylic acid methyl ester V is obtained; adjusting the pH value of the aqueous layer to 1-5 with hydrochloric acid and extracting it once or twice through the organic solvent with a weight-to-volume ratio of 1-20 times; drying it with anhydrous magnesium sulfate or anhydrous sodium sulfate and then filtering out the drying agent; concentrating the organic solvent up to a volume of 1-5 times under reduced pressure at $40°$ C.-$50°$ C.; then cooling it to $-5°$ C.-$5°$ C. for crystallization, filtering, drying at $40°$ C. under vacuum condition, thus, 1-substituted-1H-1,2,3-triazole-4-carboxylic acid I is obtained;

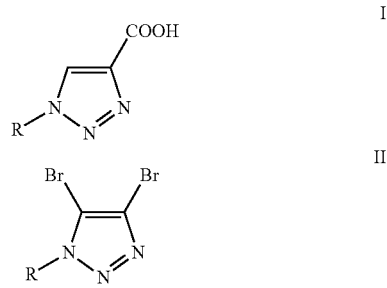

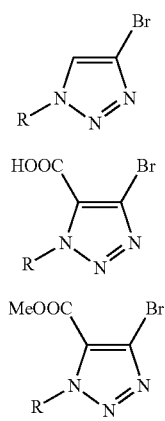

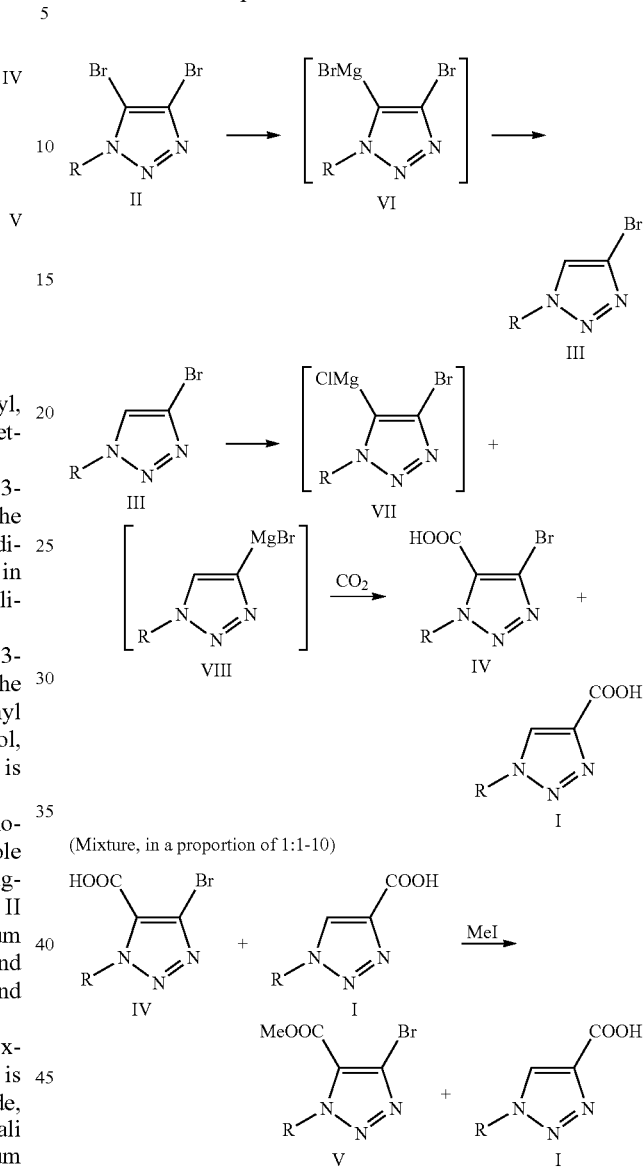

(Mixture, in a proportion of 1:1-10)

In above structural formula, R can be alkyl, aryl, aralkyl, naphthenic base, naphthenic based alkyl, heteroaryl, heteroaryl alkyl or heterocyclic alkyl.

In the preparation method for 1-substituted-1H-1,2,3-triazole-4-carboxylic acid disclosed by the Invention, the preparation method for compound 1-substituted-4,5-dibromo-1H-1,2,3-triazole II has been described in details in the Patent Application No. 201210051904.8 of the Applicant.

In the preparation method for 1-substituted-1H-1,2,3-triazole-4-carboxylic acid disclosed by the Invention, the low alcohol of $C_1$-$C_4$ in step 1) is selected from methyl alcohol, ethyl alcohol, n-propyl alcohol, isopropyl alcohol, n-butyl alcohol and tert-butyl alcohol; methyl alcohol is preferred.

The mole ratio of compound 1-substituted-4,5-dibromo-1H-1,2,3-triazole II and low alcohol is 1:0.8-1.2; the mole ratio of compound II and Grignard reagent isopropylmagnesium chloride is 1:0.8-1.5; the mole ratio of compound II and Grignard reagent isopropylmagnesium chloride-lithium chloride composite is 1:0.8-1.5 and mole ratio of compound II and carbon dioxide is 1:1-10; the mole ratio of compound II and methyl iodide is 1:0.1-1; 1:0.2-0.5 is preferred.

The inorganic alkali in Step 2) is an alkali metal hydroxide or an alkali carbonate; the alkali metal hydroxide is selected from potassium hydroxide, sodium hydroxide, lithium hydroxide and barium hydroxide; while the alkali carbonate is selected from sodium carbonate, potassium carbonate, cesium carbonate, lithium carbonate, sodium bicarbonate and potassium bicarbonate; potassium carbonate is preferred.

The organic alkali in Step 2) is selected from diethylamine, triethylamine, triethylene diamine, N-methylmorpholine, pyridine, 4-methylpyridine and 4-dimethylamine pyridine.

In the preparation method for 1-substituted-1H-1,2,3-triazole-4-carboxylic acid disclosed by the Invention, the proportion of the mixture of 1-substituted-1H-1,2,3-triazole-4-carboxylic acid and 1-substituted-4-bromo-1H-1,2,3-triazole-5-carboxylic acid prepared in Step 1) is 1-10:1.

As for said mixture of 1-substituted-1H-1,2,3-triazole-4-carboxylic acid and 1-substituted-4-bromo-1H-1,2,3-triazole-5-carboxylic acid in Step 1), due to the structural differences of the compounds, the mixture will have selective methylation reaction with methyl iodide, i.e., 1-substituted-4-bromo-1H-1,2,3-triazole-5-carboxylic acid will react with methyl iodide to generate 1-substituted-1H-1,2,3-triazole-4-carboxylic acid methyl ester, while 1-substituted-1H-1,2,3-triazole-4-carboxylic acid will not, thus the two are separated and purified.

The reaction equation is as follows:

(The separation is realized through this step).

The 1-substituted-1H-1,2,3-triazole-4-carboxylic acid I of the Invention can be prepared through the method that uses compound II as the raw material to generate compound III for separation and purification, comprising the following steps as:

(1) Dissolving 1-substituted-4,5-dibromo-1H-1,2,3-triazole II in THF/METHF with a mass-to-volume ratio of 1:2-50 and cooling it to −78° C.-0° C.; adding a Grignard reagent isopropylmagnesium chloride (the mole ratio of compound II and Grignard reagent isopropylmagnesium chloride is 1:0.8-1.5) and stirring for 0.5-2 h; adding hydrochloric acid (the mole ratio of compound II and hydrochloric acid is 1:1-20); extracting it once or twice through the organic solvent with a weight-to-volume ratio of 1-20 times; drying it with anhydrous magnesium sulfate or anhydrous sodium sulfate and filtering out the drying agent, and then concentrating it up to a volume of 1-5 times under reduced pressure at 40° C.-50° C.; then cooling it to −5° C.-5° C. for crystallization and filtration and filtering out the drying agent; drying the organic solvent at 40° C. under vacuum condition, thus, 1-substituted-4-bromo-1H-1,2,3-triazole III is obtained;

(2) Dissolving compound III in THF/METHF with a weight-to-volume ratio of 1-10 times; adding a Grignard reagent isopropylmagnesium chloride-lithium chloride composite; heating up to 10° C.-50° C. and stirring for 0.5-2 h; cooling it to −30° C.-0° C.; inletting carbon dioxide for 5-30 min and heating up to 20° C.-25° C.; adjusting pH value to 1-5 with hydrochloric acid and then extracting it once or twice through the organic solvent with a weight-to-volume ratio of 1-20 times; drying it with anhydrous magnesium sulfate or anhydrous sodium sulfate and filtering out the drying agent, and concentrating it up to dryness under reduced pressure at 40° C.-50° C., thus a mixture of 1-substituted-1H-1,2,3-triazole-4-carboxylic acid I and 1-substituted-4-bromo-1H-1,2,3-triazole-5-carboxylic acid IV is obtained;

(3) Dissolving the mixture of 1-substituted-1H-1,2,3-triazole-4-carboxylic acid I and 1-substituted-4-bromo-1H-1,2,3-triazole-5-carboxylic acid IV obtained in Step (2) in the mixed solvent of THF/METHF and N,N-dimethylformamide/N,N-dimethylacetamide with a volume ratio of 1-99%:99-1%; adding inorganic or organic alkali and methyl iodide for reaction at 0° C.-80° C. for 5-48 h; after the reaction, adding water and organic solvent at 20° C.-25° C. for layering; drying the organic layer with anhydrous magnesium sulfate or anhydrous sodium sulfate and then concentrating the it up to dryness under reduced pressure at 40° C.-50° C., thus 1-substituted-4-bromo-1H-1,2,3-triazole-5-carboxylic acid methyl ester V is obtained; adjusting the pH value of the aqueous layer to 1-5 with hydrochloric acid and extracting it through the organic solvent with a weight-to-volume ratio of 1-20 times; drying it with anhydrous magnesium sulfate or anhydrous sodium sulfate and then concentrating it up to a volume of 1-5 times under reduced pressure at 40° C.-50° C.; then cooling it to −5° C.-5° C. for crystallization, filtering, drying at 40° C. under vacuum condition, thus, 1-substituted-1H-1,2,3-triazole-4-carboxylic acid I is obtained;

The organic solvent of the Invention is a mixture of one or more of the esters or ethers of fatty acids, including one or more of ethyl formate, propyl formate, butyl formate, methyl acetate, ethyl acetate, propyl acetate, butyl acetate, acetic acid isopropyl ester, acetic acid isobutyl ester, amyl acetate, isoamyl acetate, methyl propionate, ethyl propionate, propyl propionate or buty propionate and amyl propionate, diethyl ether, propyl ether, isopropyl ether or methyl tertiary butyl ether that are mixed with a volume ratio of 1-99%:99-1%.

With the advantages as high yield, high efficient, simple operation, small equipment investment, low costs and less environmental pollution, the preparation method for 1-substituted-1H-1,2,3-triazole-4-carboxylic acid of the Invention is suitable for industrialized production and has a greater application value.

DETAILED DESCRIPTION OF THE PREFERRED EMBODIMENTS

The Invention will be further described in combination with following embodiments, which are not limitations to the application scope of the Invention.

The reagents and raw materials used in the following embodiments are purchased from the market.

Embodiment 1

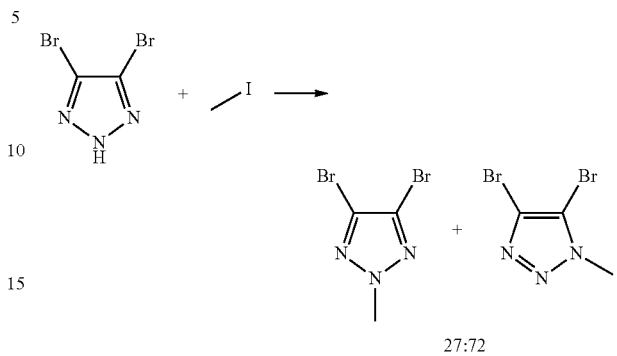

27:72

Dissolving 10.0 g (44.1 mmol) of 1-methyl-4,5-dibromo-2H-1,2,3-triazole (purchased from the market) in 90 ml THF; adding 6.1 g (44.2 mmol) of potassium carbonate; cooling it to −10° C. and adding 7.5 g (53 mmol) of methyl iodide for reaction at 35°-40° C. till the reaction is done; adding 50 ml of water to remove the THF through evaporation; extracting it with 90 ml of methyl tertiary butyl ether, drying it with anhydrous magnesium sulfate and concentrating it up to dryness under reduced pressure; adding 10 ml of methyl tertiary butyl ether into the residual solid and adding 70 ml of n-hexane slowly for solid precipitation; then string it for 1-2 h under ambient temperature; filtering; then 5.8 g of pure 1-methyl-4,5-dibromo-1H-1,2,3-triazole is obtained; the yield is 57%.

$^1$H NMR (CDCl$_3$, 400 MHz) δ 4.06 (s, 3H); $^{13}$C NMR (CDCl$_3$, 400 MHz) δ 123.0, 113.1, 37.0.

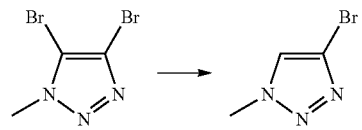

Dissolving 2.0 g (8.30 mmol) of 1-methyl-4,5-dibromo-1H-1,2,3-triazole in 15 ml THF and cooling it to −10° C.; adding 4.77 ml (9.55 mmol) of 2.0M isopropylmagnesium chloride/THF solution (purchased from the market with a concentration of 2.0M) by drops; adding 15 ml of hydrochloric acid; extracting it with 20 ml of methyl tertiary butyl ether; drying the extract liquor with anhydrous magnesium sulfate and concentrating it up to 5 ml under reduced pressure; cooling it to 0° C.-5° C. for crystallization, filtering, drying at 40° C. under vacuum condition, thus 1.55 g of 1-methyl-4-bromo-1H-1,2,3-triazole is obtained; the yield is 90%.

$^1$H NMR (CDCl$_3$, 400 MHz) δ 7.61 (s, 1H), 4.13 (s, 3H); $^{13}$C NMR (CDCl$_3$, 400 MHz) δ 124.8, 120.5, 37.3;

Embodiment 2

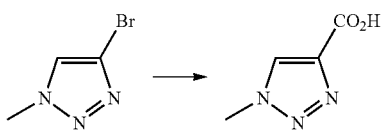

Dissolving 1.50 g (9.26 mmol) of 1-methyl-4-bromo-1H-1,2,3-triazole (obtained in Embodiment 1) in 15 ml THF; adding 8.19 ml (10.65 mmol) of isopropylmagnesium chloride-lithium chloride composite (1.3M solution of THF) by drops at 0° C. for continuous reaction at 10° C.-16° C. for 1 h; cooling the reaction mixture to −10° C.; inletting carbon dioxide for 10 min; adding 7 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 10 ml THF/1.5 ml DMF (dimethyl formamide); adding 1.28 g (9.26 mmol) of potassium carbonate and 526 mg (3.70 mmol) of methyl iodide for reaction at 20° C.-30° C. for 48 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C. and cooling it to 0° C. for crystallization, filtering, and drying at 40° C. under vacuum condition, thus, 576 mg of 1-methyl-1H-1,2,3-triazole-4-carboxylic acid is obtained; the yield is 49%.

$^1$H NMR (CD$_3$COCD$_3$, 400 MHz) δ 8.46 (s, 1H), 4.20 (s, 1H).

Embodiment 3

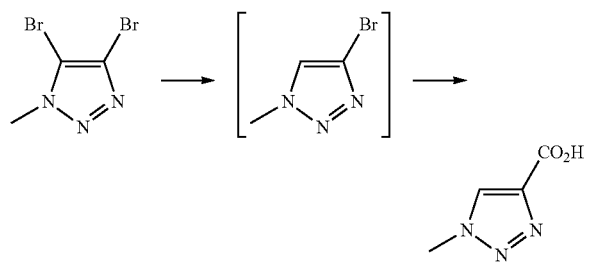

Dissolving 2.0 g (8.30 mmol) of 1-methyl-4,5-dibromo-1H-1,2,3-triazole in 15 ml THF and cooling it to −20° C.; adding 4.77 ml (9.55 mmol) of 2.0M isopropylmagnesium chloride/THF solution by drops for continuous reaction for 1 h; adding 0.39 ml (9.55 mmol) of methyl alcohol by drops; adding 8.19 ml (10.65 mmol) of isopropylmagnesium chloride-lithium chloride composite (isopropylmagnesium chloride-lithium chloride composite dissolved in 1.3M solution of THF; purchased from the market with a concentration of 1.3M) by drops at 0° C. for continuous reaction at 10° C.-16° C. for 1 h; cooling the reaction mixture to −10° C.; inletting carbon dioxide for 10 min; adding 7 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 10 ml THF/1.5 ml DMF; adding 1.14 g (8.30 mmol) of potassium carbonate and 471 mg (3.32 mmol) of methyl iodide for reaction at 20° C.-30° C. for 48 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C. and cooling it to 0° C. for crystallization, filtering, and drying at 40° C. under vacuum condition, thus, 587 mg of 1-methyl-1H-1,2,3-triazole-4-carboxylic acid is obtained; the yield is 50%.

$^1$H NMR (CD$_3$COCD$_3$, 400 MHz) δ 8.46 (s, 1H), 4.20 (s, 1H).

Embodiment 4

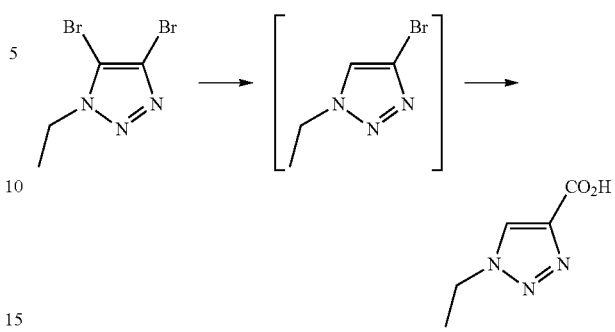

Dissolving 2.30 g (9.02 mmol) of 1-ethyl-4,5-dibromo-1H-1,2,3-triazole (prepared through the method according to Embodiment 1 with the raw material of ethyl bromide) in 15 ml THF and cooling it to −30° C.; adding 5.19 ml (10.38 mmol) of 2.0M isopropylmagnesium chloride/THF solution (purchased from the market) by drops for continuous reaction for 1 h; adding 0.42 ml (10.38 mmol) of methyl alcohol by drops; adding 9.18 ml (11.94 mmol) of isopropylmagnesium chloride-lithium chloride composite (1.3M isopropylmagnesium chloride-lithium chloride composite dissolving in THF; purchased from the market with a concentration of 1.3M) by drops at −10° C. for continuous reaction at 0° C.-15° C. for 1 h; cooling the reaction mixture to −10° C.; inletting carbon dioxide for 10 min; adding 10 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 20 ml THF/1.5 ml DMF; adding 1.24 g (9.02 mmol) of potassium carbonate and 509 mg (3.60 mmol) of methyl iodide for reaction at 20° C.-30° C. for 48 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, and drying at 40° C. under vacuum condition, thus, 675 mg of 1-ethyl-1H-1,2,3-triazole-4-carboxylic acid is obtained; the yield is 53%.

$^1$H NMR (DMSO-d$_6$, 400 MHz) δ 8.69 (s, 1H), 4.43 (q, J=7.2 Hz, 2H), 1.45 (t, J=7.2 Hz, 3H); $^{13}$C NMR ((DMSO-d$_6$, 400 MHz) δ 161.7, 139.6, 128.3, 44.9, 15.1.

Embodiment 5

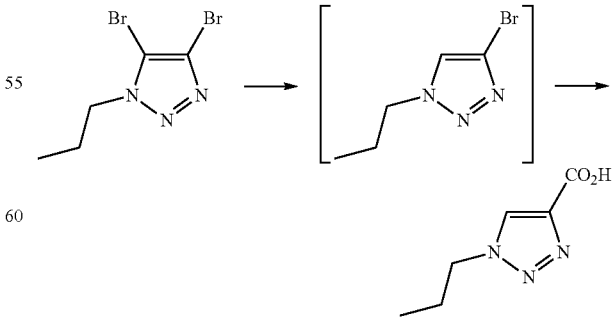

Dissolving 2.40 g (8.92 mmol) of 1-n-propyl-4,5-dibromo-1H-1,2,3-triazole (prepared through the method according to Embodiment 1 with the raw material of n-propyl bromide) in 15 ml METHF and cooling it to −30° C.; adding 5.13 ml (10.26 mmol) of 2.0M isopropylmagnesium chloride/THF solution by drops for continuous reaction for 1 h; adding 0.42 ml (10.38 mmol) of ethyl alcohol by drops; adding 9.18 ml (11.94 mmol) of isopropylmagnesium chloride-lithium chloride composite (1.3M solution of THF; purchased from the market) by drops at −10° C. for continuous reaction at 5° C.-15° C. for 1 h; cooling the reaction mixture to −10° C.; inletting carbon dioxide for 15 min; adding 10 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 20 ml THF/1.5 ml DMF; adding 1.23 g (8.92 mmol) of potassium carbonate and 497 mg (3.50 mmol) of methyl iodide for reaction at 30° C.-40° C. for 24 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, drying at 40° C. under vacuum condition, thus, 675 mg of 1-n-propyl-1H-1,2,3-triazole-4-carboxylic acid is obtained; the yield is 53%.

$^1$H NMR (DMSO-$d_6$, 400 MHz) δ 13.04 (bs, 1H), 8.69 (s, 1H), 4.37 (t, J=7.2 Hz, 2H), 1.89-1.83 (m, 2H), 0.84 (t, J=7.2 Hz, 3H); $^{13}$C NMR (DMSO-$d_6$, 400 MHz) δ 161.7, 139.6, 128.7, 51.1, 22.9, 10.6.

Embodiment 6

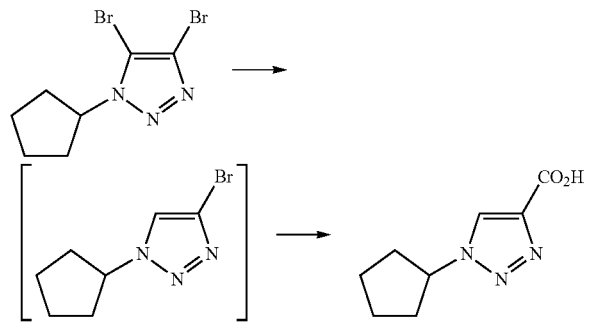

Dissolving 2.50 g (8.48 mmol) of 1-cyclopentyl-4,5-dibromo-1H-1,2,3-triazole (prepared through the method according to Embodiment 1 with the raw material of cyclopentyl chloride) in 15 ml THF and cooling it to −20° C.; adding 4.87 ml (9.75 mmol) of 2.0M isopropylmagnesium chloride/THF solution by drops for continuous reaction for 1 h; adding 0.40 ml (9.75 mmol) of ethyl alcohol by drops; adding 7.50 ml (9.75 mmol) of isopropylmagnesium chloride-lithium chloride composite (1.3M solution of THF; purchased from the market) by drops at −10° C. for continuous reaction at 10° C.-20° C. for 1 h; cooling the reaction mixture to −10° C.; inletting carbon dioxide for 15 min; adding 15 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 20 ml THF/1.5 ml DMF; adding 1.17 g (8.48 mmol) of potassium carbonate and 482 mg (3.40 mmol) of methyl iodide for reaction at 25° C.-40° C. for 24 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, drying at 40° C. under vacuum condition, thus, 937 mg of 1-cyclopentyl-1H-1,2,3-triazole-4-carboxylic acid is obtained; the yield is 61%.

$^1$H NMR (DMSO-$d_6$, 400 MHz) δ 13.04 (bs, 1H), 8.72 (s, 1H), 5.01-5.10 (m, 1H), 2.24-2.15 (m, 2H), 2.03-1.94 (m, 2H), 1.86-1.77 (m, 2H), 1.73-1.67 (m, 2H); $^{13}$C NMR (DMSO-$d_6$, 400 MHz) δ 161.8, 139.6, 127.6, 61.4, 32.7, 23.6.

Embodiment 7

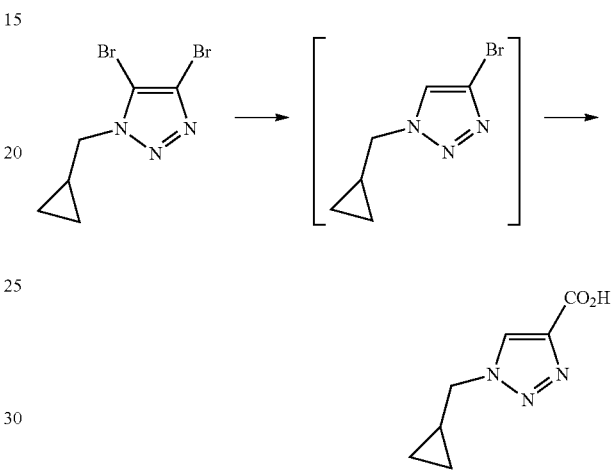

Dissolving 2.50 g (8.90 mmol) of 1-cyclopropyl methyl-4,5-dibromo-1H-1,2,3-triazole (prepared through the method according to Embodiment 1 with the raw material of cylopropylmethyl chloride) in 15 ml THF and cooling it to −20° C.; adding 4.87 ml (9.75 mmol) of 2.0M isopropyl-magnesium chloride/THF solution by drops for continuous reaction for 1 h; adding 0.40 ml (9.75 mmol) of methyl alcohol by drops; adding 7.50 ml (9.75 mmol) of isopropylmagnesium chloride-lithium chloride composite (1.3M solution of THF; purchased from the market) by drops at −10° C. for continuous reaction at 10° C.-20° C. for 1 h; cooling the reaction mixture to −10° C.; inletting carbon dioxide for 15 min; adding 15 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 20 ml THF/1.5 ml DMF; adding 1.17 g (8.48 mmol) of potassium carbonate and 482 mg (3.40 mmol) of methyl iodide for reaction at 25° C.-40° C. for 24 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, drying at 40° C. under vacuum condition, thus, 952 mg of 1-cyclopropyl methyl-1H-1,2,3-triazole-4-carboxylic acid is obtained; the yield is 64%.

$^1$H NMR (CD$_3$COCD$_3$, 400 MHz) δ 8.57 (s, 1H), 4.37 (d, J=7.6 Hz, 2H), 1.34-1.38 (m, 1H), 0.68-0.64 (m, 2H), 0.56-0.50 (m, 2H); $^{13}$C NMR (CD$_3$COCD$_3$, 400 MHz) δ 162.1, 140.6, 128.8, 55.5, 12.0, 4.3.

Embodiment 8

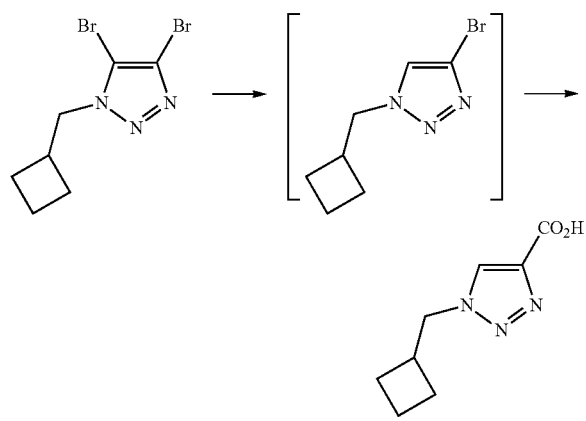

Dissolving 2.50 g (8.48 mmol) of 1-cyclobutyl methyl-4,5-dibromo-1H-1,2,3-triazole (prepared through the method according to Embodiment 1 with the raw material of cyclobutylmethyl chloride) in 15 ml THF and cooling it to −20° C.; adding 4.87 ml (9.75 mmol) of 2.0M isopropylmagnesium chloride/THF solution by drops for continuous reaction for 1 h; adding 0.40 ml (9.75 mmol) of methyl alcohol by drops; adding 7.50 ml (9.75 mmol) of isopropylmagnesium chloride-lithium chloride composite (1.3M solution of THF; purchased from the market) by drops at −10° C. for continuous reaction at 10° C.-20° C. for 1 h; cooling the reaction mixture to −10° C.; inletting carbon dioxide for 15 min; adding 15 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 20 ml THF/1.5 ml DMF; adding 1.17 g (8.48 mmol) of potassium carbonate and 482 mg (3.40 mmol) of methyl iodide for reaction at 25° C.-40° C. for 24 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, drying at 40° C. under vacuum condition, thus, 1.07 g of 1-cyclobutyl methyl-1H-1,2,3-triazole-4-carboxylic acid is obtained; the yield is 70%.

$^1$H NMR (CD$_3$COCD$_3$, 400 MHz) δ 8.47 (s, 1H), 4.51 (d, J=7.6 Hz, 2H), 2.96-2.88 (m, 1H), 2.103-2.05 (m, 2H), 1.98-1.88 (m, 4H); $^{13}$C NMR (CD$_3$COCD$_3$, 400 MHz) δ 162.8, 141.0, 129.0, 55.7, 36.4, 26.1, 18.5.

Embodiment 9

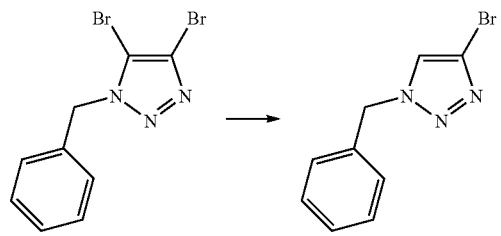 [SMILES: Brc1nnn(Cc2ccccc2)c1Br ; Brc1cn(Cc2ccccc2)nn1]

Dissolving 2.0 g (6.31 mmol) of 1-benzyl-4,5-dibromo-1H-1,2,3-triazole (prepared through the method according to Embodiment 1 with the raw material of benzyl chloride) in 15 ml METHF and cooling it to −20° C.; adding 3.63 ml (7.26 mmol) of 2.0M isopropylmagnesium chloride/THF solution by drops; adding 15 ml of hydrochloric acid; extracting it with methyl tertiary butyl ether; drying the extract liquor with anhydrous magnesium sulfate and concentrating it up to 5 ml under reduced pressure at 40° C.-50° C.; cooling it to 0° C. for crystallization, filtering, drying at 40° C. under vacuum condition, thus 1.43 g of 1-benzyl-4-bromo-1H-1,2,3-triazole is obtained; the yield is 95%.

$^1$H NMR (CDCl$_3$, 400 MHz) δ 7.48 (s, 1H), 7.39 (m, 3H), 7.28 (m, 2H), 5.52 (s, 2H); $^{13}$C NMR (CDCl$_3$, 400 MHz) δ 133.9, 129.3, 129.1, 128.2, 123.7, 120.8, 54.9.

Embodiment 10

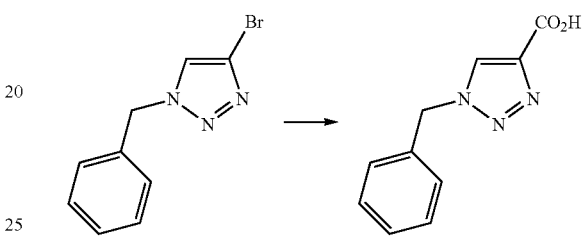

Dissolving 1.40 g (5.88 mmol) of 1-benzyl-4-bromo-1H-1,2,3-triazole in 10 ml THF; adding 5.20 ml (6.76 mmol) of isopropylmagnesium chloride-lithium chloride composite (1.3M solution of THF) by drops at 0° C. for continuous reaction at 10° C.-30° C. for 1 h; cooling the reaction mixture to −10° C.; inletting carbon dioxide for 10 min; adding 10 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 10 ml THF/1.5 ml DMF; adding 811 mg (5.88 mmol) of potassium carbonate and 334 mg (2.35 mmol) of methyl iodide for reaction at 20° C.-30° C. for 48 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, drying at 40° C. under vacuum condition, thus, 731 mg of 1-benzyl-1H-1,2,3-triazole-4-carboxylic acid is obtained; the yield is 61%.

$^1$H NMR (CD$_3$COCD$_3$, 400 MHz) δ 8.54 (s, 1H), 7.42-7.34 (m, 5H), 5.72 (s, 2H); $^{13}$C NMR (CD$_3$COCD$_3$, 400 MHz) δ 162.5, 141.3, 136.6, 129.8, 129.3, 129.2, 129.1, 54.4.

Embodiment 11

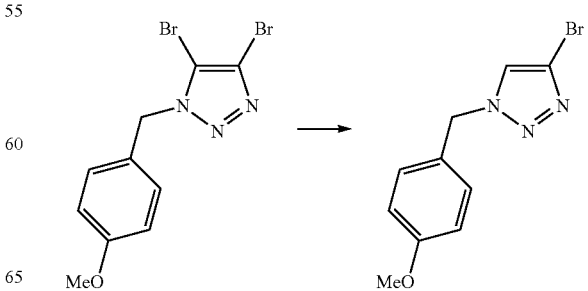

Dissolving 2.5 g (7.20 mmol) of 1-p-methoxybenzyl-4,5-dibromo-1H-1,2,3-triazole (prepared through the method according to Embodiment 1 with the raw material of p-methoxybenzyl chloride) in 20 ml THF and cooling it to −10° C.; adding 4.14 ml (8.29 mmol) of 2.0M isopropylmagnesium chloride/THF solution by drops; adding 15 ml of hydrochloric acid; extracting it with 20 ml of methyl tertiary butyl ether; drying the extract liquor with anhydrous magnesium sulfate and concentrating it up to 5 ml under reduced pressure at 40° C.-50° C.; cooling it to 0° C. for crystallization, filtering, drying at 40° C. under vacuum condition, thus 1.83 g of 1-p-methoxybenzyl-4,5-dibromo-1H-1,2,3-triazole is obtained; the yield is 95%.

$^1$H NMR (CDCl$_3$, 400 MHz) δ 7.38 (s, 1H), 7.14 (ABq, J=8.4 Hz, 2H), 6.80 (ABq, J=8.4 Hz, 2H), 5.35 (s, 2H), 3.71 (s, 3H); $^{13}$C NMR (CDCl$_3$, 400 MHz) δ 160.1, 129.8, 125.8, 123.5, 120.7, 114.6, 55.4, 54.4.

Embodiment 12

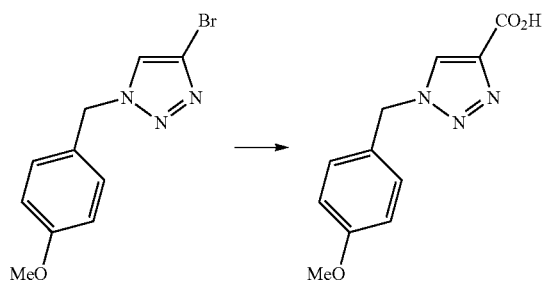 [SMILES: COc1ccc(Cn2cc(Br)nn2)cc1 ; COc1ccc(Cn2cc(C(=O)O)nn2)cc1]

Dissolving 1.70 g (6.34 mmol) of 1-p-methoxybenzyl-4-bromo-1H-1,2,3-triazole in 10 ml THF; adding 5.61 ml (7.29 mmol) of isopropylmagnesium chloride-lithium chloride composite (1.3M solution of THF) by drops at 0° C. for continuous reaction at 10° C.-30° C. for 1 h; Adding 10 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 15 ml THF/1.5 ml DMF; adding 875 mg (6.34 mmol) of potassium carbonate and 334 mg (2.35 mmol) of methyl iodide for reaction at 20° C.-30° C. for 48 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, drying at 40° C. under vacuum condition, thus, 1.06 g of 1-p-methoxybenzyl-1H-1,2,3-triazole-4-carboxylic acid is obtained; the yield is 72%.

$^1$H NMR (DMSO-d$_6$, 400 MHz) δ 13.10 (bs, 1H), 8.73 (s, 1H), 7.34 (ABq, J=8.4 Hz, 2H), 6.94 (ABq, J=8.4 Hz, 2H), 5.57 (s, 2H), 3.74 (s, 3H); $^{13}$C NMR (DMSO-d$_6$, 400 MHz) δ 161.6, 159.2, 139.8, 129.7, 128.6, 127.5, 114.1, 55.1, 52.6.

Embodiment 13

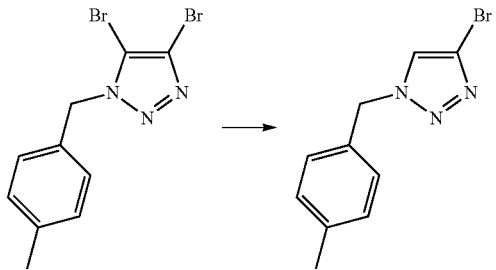

Dissolving 2.5 g (7.55 mmol) of 1-p-methylbenzyl-4,5-dibromo-1H-1,2,3-triazole (prepared through the method according to Embodiment 1 with the raw material of p-methylbenzyl chloride) in 20 ml THF and cooling it to −10° C.; adding 4.34 ml (8.69 mmol) of 2.0M isopropylmagnesium chloride/THF solution by drops; adding 10 ml of hydrochloric acid; extracting it with 20 ml of methyl tertiary butyl ether; drying the extract liquor with anhydrous magnesium sulfate and concentrating it up to 5 ml under reduced pressure at 40° C.-50° C.; cooling it to 0° C. for crystallization, filtering, drying at 40° C. under vacuum condition, thus 1.88 g of 1-p-methylbenzyl-4-bromo-1H-1,2,3-triazole is obtained; the yield is 99%.

$^1$H NMR (CDCl$_3$, 400 MHz) δ 7.43 (s, 1H), 7.19 (ABq, J=8.8 Hz, 2H), 7.17 (ABq, J=8.8 Hz, 2H), 5.57 (s, 2H), 2.35 (s, 3H); $^{13}$C NMR (CDCl$_3$, 400 MHz) δ 139.1, 130.8, 129.9, 128.3, 123.5, 120.8, 54.7, 21.2.

Embodiment 14

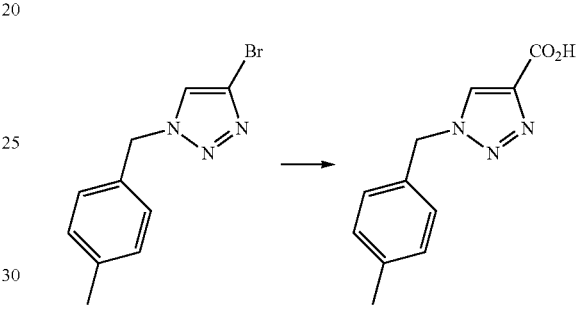

Dissolving 1.80 g (7.14 mmol) of 1-p-methylbenzyl-4-bromo-1H-1,2,3-triazole in 10 ml THF; adding 6.32 ml (8.21 mmol) of isopropylmagnesium chloride-lithium chloride composite (1.3M solution of THF) by drops at 0° C. for continuous reaction at 10° C.--30° C. for 1 h; cooling the reaction mixture to −10° C.; inletting carbon dioxide for 10 min; adding 10 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 15 ml THF/1.5 ml DMF; adding 985 mg (7.14 mmol) of potassium carbonate and 355 mg (2.50 mmol) of methyl iodide for reaction at 20° C.-30° C. for 48 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, drying at 40° C. under vacuum condition, thus, 1.08 g of 1-p-methylbenzyl-1H-1,2,3-triazole-4-carboxylic acid is obtained; the yield is 70%.

$^1$H NMR (DMSO-d$_6$, 400 MHz) δ 13.08 (bs, 1H), 8.74 (s, 1H), 7.25 (ABq, J=8.0 Hz, 2H), 7.19 (ABq, J=8.0 Hz, 2H), 5.60 (s, 2H), 2.29 (s, 3H); $^{13}$C NMR (DMSO-d$_6$, 400 MHz) δ 161.6, 139.8, 137.6, 132.6, 129.3, 128.8, 128.0, 52.8, 20.7.

Embodiment 15

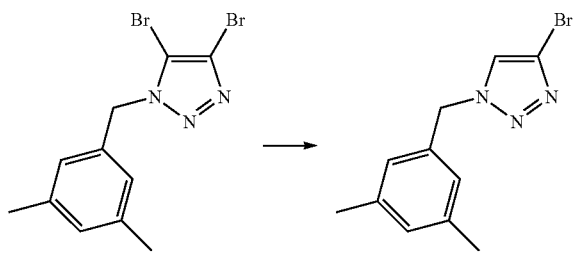 [SMILES: Cc1cc(C)cc(Cn2nnc(Br)c2Br)c1 ; Cc1cc(C)cc(Cn2cc(Br)nn2)c1]

Dissolving 1.04 g (3.01 mmol) of 1-(3,5-dimethylbenzyl)-4,5-dibromo-1H-1,2,3-triazole (prepared through the method according to Embodiment 1 with the raw material of 3,5-dimethylbenzyl chloride) in 10 ml THF and cooling it to −10° C.; adding 1.73 ml (3.47 mmol) of 2.0M isopropylmagnesium chloride/THF solution by drops; adding 5 ml of hydrochloric acid; extracting it with 20 ml of methyl tertiary butyl ether; drying the extract liquor with anhydrous magnesium sulfate and concentrating it up to 5 ml under reduced pressure at 40° C.-50° C.; cooling it to 0° C. for crystallization, filtering, drying at 40° C. under vacuum condition, thus 782 mg of 1-(3,5-dimethylbenzyl)-4-bromo-1H-1,2,3-triazole is obtained; the yield is 98%.

$^1$H NMR (CDCl$_3$, 400 MHz) δ 7.44 (s, 1H), 6.99 (s, 1H), 6.88 (s, 2H), 5.42 (s, 2H), 2.29 (s, 6H); $^{13}$C NMR (CDCl$_3$, 400 MHz) δ 139.0, 133.6, 130.7, 126.1, 123.6, 120.8, 54.9, 21.2.

Embodiment 16

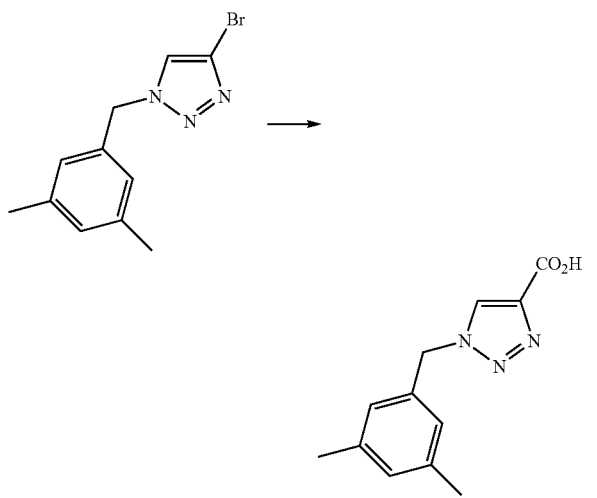

Dissolving 752 mg (2.83 mmol) of 1-(3,5-dimethylbenzyl)-4-bromo-1H-1,2,3-triazole in 10 ml of tetrahydrofuran; adding 2.50 ml (3.25 mmol) of isopropylmagnesium chloride-lithium chloride composite (1.3M solution of THF; purchased from the market) by drops at 0° C. for continuous reaction at 10° C.-30° C. for 1 h; cooling the reaction mixture to −10° C.; inletting carbon dioxide for 10 min; adding 5 ml of hydrochloric acid; extracting it with 30 ml of ethyl acetate; drying the extract liquor with anhydrous sodium sulfate and concentrating it up to dryness under reduced pressure at 40° C.-50° C. to obtain a crude product; dissolving the crude product in 10 ml THF/1 ml DMF; adding 390 mg (3.83 mmol) of potassium carbonate and 160 mg (1.13 mmol) of methyl iodide for reaction at 20° C.-30° C. for 24 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, drying at 40° C. under vacuum condition, thus, 419 mg of 1-(3,5-dimethylbenzyl)-1H-1,2,3-triazole-4-carboxylic acid is obtained; the yield is 64%.

$^1$H NMR (DMSO-d$_6$, 400 MHz) δ 13.12 (bs, 1H), 8.75 (s, 1H), 6.96 (s, 3H), 5.56 (s, 2H), 2.24 (s, 6H); $^{13}$C NMR (DMSO-d$_6$, 400 MHz) δ 161.6, 139.8, 137.9, 135.3, 129.6, 128.9, 125.7, 53.0, 20.7.

Embodiment 17

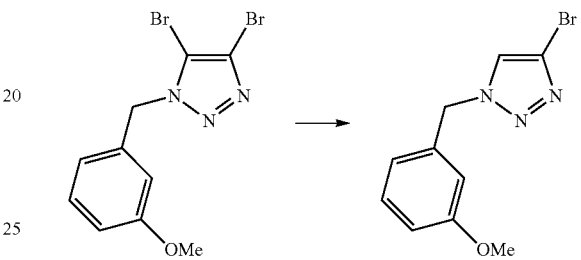

Dissolving 2.4 g (6.92 mmol) of 1-m-methoxybenzyl-4,5-dibromo-1H-1,2,3-triazole (prepared through the method according to Embodiment 1 with the raw material of m-methoxybenzyl chloride) in 20 ml THF and cooling it to −10° C.; adding 4.14 ml (8.29 mmol) of 2.0M isopropylmagnesium chloride/THF solution by drops; adding 15 ml of hydrochloric acid; extracting it with 20 ml of methyl tertiary butyl ether; drying the extract liquor with anhydrous magnesium sulfate and concentrating it up to 5 ml under reduced pressure at 40° C.-50° C.; cooling it to 0° C. for crystallization, filtering, drying at 40° C. under vacuum condition, thus 1.78 g of 1-m-methoxybenzyl-4-bromo-1H-1,2,3-triazole is obtained; the yield is 96%.

$^1$H NMR (CDCl$_3$, 400 MHz) δ 7.48 (s, 1H), 7.30 (t, J=8.0 Hz, 1H), 6.90 (dd, J=2.4, 8.0 Hz, 1H), 6.85 (d, J=7.6 Hz, 1H), 6.80 (s, 1H), 5.48 (s, 2H), 3.79 (s, 3H); $^{13}$C NMR (CDCl$_3$, 400 MHz) δ 160.2, 135.2, 130.4, 123.7, 120.8, 120.43, 114.5, 113.9, 55.4, 54.8.

Embodiment 18

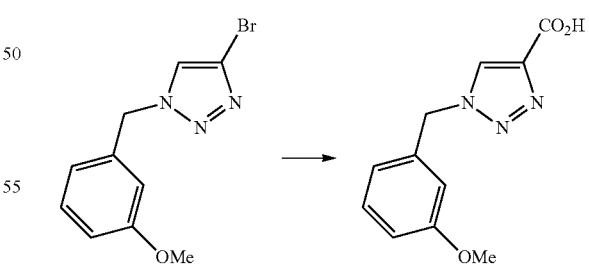

Dissolving 1.70 g (6.34 mmol) of 1-m-methoxybenzyl-4-bromo-1H-1,2,3-triazole in 10 ml THF; adding 5.61 ml (7.29 mmol) of isopropylmagnesium chloride-lithium chloride composite (1.3M solution of THF; purchased from the market) by drops at 0° C. for continuous reaction at 10° C.-30° C. for 1 h; cooling the reaction mixture to −10° C.; inletting carbon dioxide for 10 min; adding 10 ml of hydrochloric acid; extracting it with 30 ml of ethyl acetate;

drying the extract liquor with anhydrous sodium sulfate and concentrating it up to dryness under reduced pressure at 40° C.-50° C. to obtain a crude product; dissolving the crude product in 15 ml THF/1.5 ml DMF; adding 875 mg (6.34 mmol) of potassium carbonate and 334 mg (2.35 mmol) of methyl iodide for reaction at 20° C.-30° C. for 48 h; adding 20 ml of water and 20 ml of ethyl acetate for layering; adjusting the pH value of the aqueous layer to 1-5 with hydrochloric acid and extracting it with 20 ml of ethyl acetate; then concentrating it up to 3 ml under reduced pressure at 40° C.-50° C. and cooling it to 0° C. for crystallization, filtering, drying at 40° C. under vacuum condition, thus, 1.03 g of 1-m-methoxybenzyl-1H-1,2,3-triazole-4-carboxylic acid is obtained; the yield is 70%.

$^1$H NMR (DMSO-$d_6$, 400 MHz) δ 8.81 (s, 1H), 7.30 (t, J=8.0 Hz, 1H), 6.96-6.89 (m (3H), 5.62 (s, 2H), 3.75 (s, 3H); $^{13}$C NMR (DMSO-$d_6$, 400 MHz) δ 161.6, 159.4, 139.9, 137.0, 130.0, 129.0, 120.1, 113.8, 113.7, 55.1, 52.9.

The above are the preferred embodiments rather than the limitations of the Invention; any amendment or equivalent replacement made to the Invention within the spirit and scope of the Invention shall be included in the protection scope of the Invention.

We claim:

1. A method for synthesizing 1-substituted-1H-1,2,3-triazole-4-carboxylic acid, comprising steps (1) and (2) as follows:

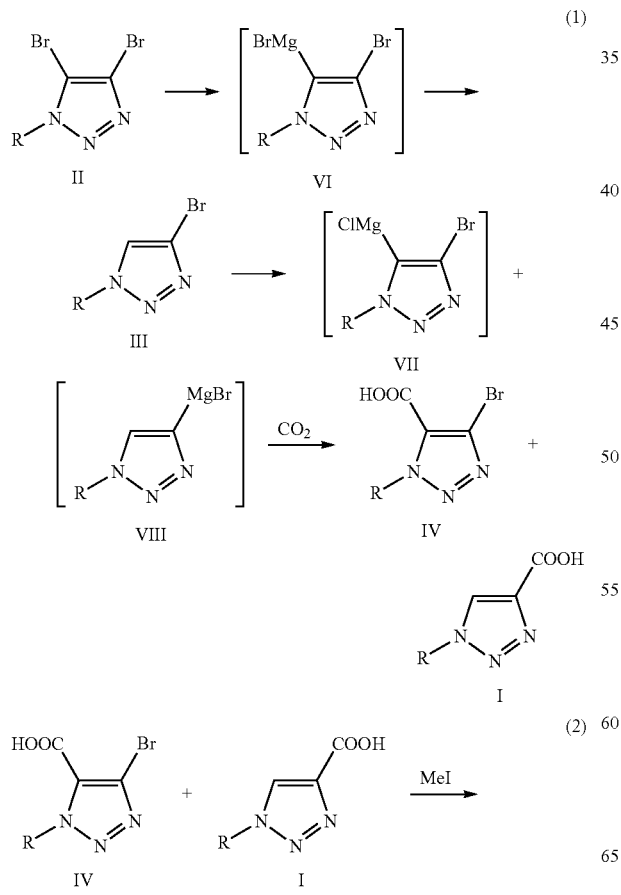

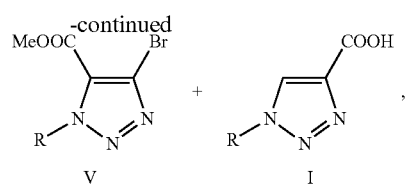

wherein R is alkyl, aryl, aralkyl, naphthenic base, naphthenic based alkyl, heteroaryl, heteroaryl alkyl or heterocyclic substituted alkyl.

2. The method of claim 1, wherein:

step (1) comprises (1a) dissolving 1-substituted-4,5-dibromo-1H-1,2,3-triazole (II) in tetrahydrofuran (THF) or methyltetrahydrofuran (METHF) with a mass-to-volume ratio of 1: 2-50 and cooled to −78° C.-0° C.; (1b) adding a Grignard reagent isopropylmagnesium chloride and stirring for 0.5-2 hours; (1c) adding an alcohol of C1-C4 to obtain 1-substituted-4-bromo-1H-1,2,3-triazole (III); (1d) adding a complex of Grignard reagent isopropylmagnesium chloride-lithium chloride; (1e) heating up to 10° C.-50° C. and stirring for 0.5-2h; (1f) cooling to −30° C.-0° C., inletting carbon dioxide for 5-30 min and heating up to 20° C.-25° C.; (1g) adjusting pH value to 1-5 with hydrochloric acid and then extracting once or twice through an organic solvent with a volume-to-weight ratio of 1-20: 1; (1h) drying with anhydrous magnesium sulfate or anhydrous sodium sulfate, filtering out the drying agent, and finally concentrating to dryness under a reduced pressure at 40° C.-50° C. to afford a mixture of 1-substituted-1H-1,2,3-triazole-4-carboxylic acid (I) and 1-substituted-4-bromo-1H-1,2,3-triazole-5-carboxylic acid (IV);

and step (2) comprises (2a) dissolving the mixture of 1-substituted-1H-1,2,3-triazole-4-carboxylic acid I and 1-substituted-4-bromo-1H-1,2,3-triazole-5-carboxylic acid IV obtained in Step 1) in a solvent mixture of THF/METHF and N,N-dimethylformamide/N,N-dimethylacetamide with a volume ratio of 1-99%: 99-1%; (2b) adding inorganic or organic alkali and methyl iodide for reaction at 0° C.-80° C. for 5-48 hours; (2c) adding a volume of a mixture of water and an organic solvent (10-1: 1-10) with a mass-to-volume ratio of 1: 1-20 at 20° C.-25° C. for layering an organic layer and an aqueous layer; (2d) drying the organic layer with anhydrous magnesium sulfate or anhydrous sodium sulfate and then concentrating to dryness under a reduced pressure at 40° C.-50° C. to afford 1-substituted-4-bromo-1H-1,2,3-triazole-5-carboxylic acid methyl ester (V); (2e) adjusting the aqueous layer to a pH value of 1-5 with hydrochloric acid and extracting by a volume of an organic solvent with a weight-to-volume ratio of 1-20 times; (2f) drying with anhydrous magnesium sulfate or anhydrous sodium sulfate and then concentrating to a volume reduced by 1-5 times under a reduced pressure at 40° C.-50° C.; and (2g) cooling it to −5° C.-5° C. for crystallization, filtering, and drying at 40° C. under a vacuum condition to afford 1-substituted-1H-1,2,3-triazole-4-carboxylic acid (I).

3. The method of claim 2, wherein the alcohol of C1-C4 in step (1) is selected from the group consisting of methyl alcohol, ethyl alcohol, n-propyl alcohol, isopropyl alcohol, n-butyl alcohol and tert-butyl alcohol.

4. The method of claim 2, wherein in step (1) 1-substituted-4,5-dibromo-1H-1,2,3-triazole (II) and the alcohol of C1-C4 has a mole ratio of 1: 0.8-1.2; 1-substituted-4,5-dibromo-1H-1,2,3-triazole (II) and the Grignard reagent isopropylmagnesium chloride has a mole ratio of 1: 0.8-1.5; 1-substituted-4,5-dibromo-1H-1,2,3-triazole (II) and the complex of Grignard reagent isopropylmagnesium chloride-lithium chloride has a mole ratio of 1: 0.8-1.5; and 1-substituted-4,5-dibromo-1H-1,2,3-triazole (II) and the carbon dioxide has a mole ratio of 1: 1-10.

5. The method of claim 2, wherein in step (2) the inorganic alkali is an alkali metal hydroxide or an alkali carbonate; the alkali metal hydroxide is selected from the group consisting of potassium hydroxide, sodium hydroxide, lithium hydroxide and barium hydroxide and the alkali carbonate is selected from the group consisting of sodium carbonate, potassium carbonate, cesium carbonate, lithium carbonate, sodium bicarbonate and potassium bicarbonate.

6. The method of claim 2, wherein in step (2) the inorganic alkali is selected from the group consisting of diethylamine, triethylamine, triethylene diamine, N-methylmorpholine, pyridine, 4-methylpyridine and 4-dimethylamine pyridine.

7. The method of claim 2, wherein 1-substituted-1H-1,2,3-triazole-4-carboxylic acid and 1-substituted-4-bromo-1H-1,2,3-triazole-5-carboxylic acid prepared has a ratio of 1-10: 1.

8. The method of claim 2, wherein in step (1) 1-substituted-4,5-dibromo-1H-1,2,3-triazole (II) and the Grignard reagent isopropylmagnesium chloride has a mole ratio of 1: 0.8-1.5 and 1-substituted-4,5-dibromo-1H-1,2,3-triazole (II) and hydrochloric acid has a mole ratio of 1: 1-20.

9. The method of claim 2, wherein the organic solvent is ethyl formate, propyl formate, butyl formate, methyl acetate, ethyl acetate, propyl acetate, butyl acetate, acetic acid isopropyl ester, acetic acid isobutyl ester, amyl acetate, isoamyl acetate, methyl propionate, ethyl propionate, propyl propionate or buty propionate and amyl propionate, diethyl ether, propyl ether, isopropyl ether or methyl tertiary butyl ether, or a mixture of two or more thereof with a volume ratio of 1%-99% : 99%-1%.

\* \* \* \* \*